United States Patent

Nedelec et al.

[11] Patent Number: 4,943,566
[45] Date of Patent: Jul. 24, 1990

[54] NOVEL 17-ARYL-STEROIDS

[75] Inventors: Lucien Nedelec, Le Raincy; Francois Nique, Pavillons-Sous-Bois; Daniel Philibert, La Varenne Saint-Hilaire; Martine Moguilewsky; Marie-Madeleine Bouton, both of Paris, all of France

[73] Assignee: Roussel Uclaf

[21] Appl. No.: 225,305

[22] Filed: Jul. 28, 1988

[30] Foreign Application Priority Data

Jul. 30, 1987 [FR] France .................. 87 10794

[51] Int. Cl.$^5$ ............... A61K 31/56; A61K 31/58; C07J 1/00; C07J 71/00
[52] U.S. Cl. ................ 514/179; 514/172; 514/177; 540/76; 552/505; 552/648; 552/502; 552/626; 552/646
[58] Field of Search ............ 514/172, 177, 179; 260/397.3, 397.45; 540/76

[56] References Cited

U.S. PATENT DOCUMENTS

| 3,502,699 | 3/1970 | Hughes et al. | 260/397.3 |
| 4,233,296 | 11/1980 | Teutsch et al. | 260/397.3 |
| 4,386,085 | 5/1983 | Teutsch | 540/76 |
| 4,477,445 | 10/1984 | Philibert et al. | 260/397.3 |

Primary Examiner—Joseph A. Lipovsky

[57] ABSTRACT

A compound selected from the group consisting of compounds of the formula

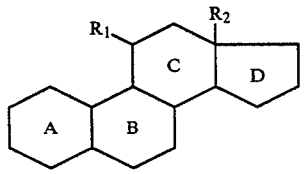

wherein $R_1$ is an organo of 1 to 18 carbon atoms optionally containing at least one heteroatom connected to the C ring by a carbon atom, $R_2$ is methyl or ethyl, the A and B rings being selected from the group consisting of

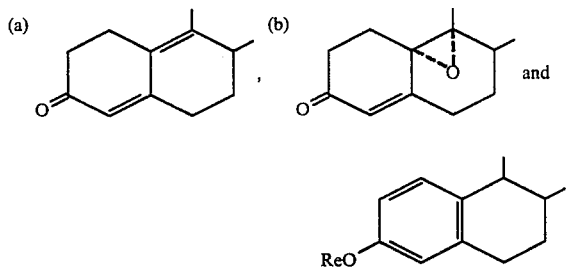

Re is selected from the group consisting of hydrogen, optionally substituted alkyl of 1 to 6 carbon atoms and acyl and the D ring is selected from the group consisting of

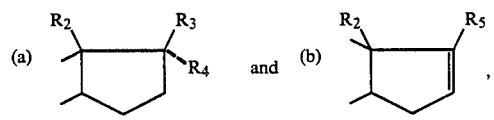

one of $R_3$ and $R_4$ is selected from the group consisting of hydroxy, protected hydroxy, acyl and alkoxy and the other is an optionally substituted aryl, $R_5$ is an optionally substituted aryl and their non-toxic, pharmaceutically acceptable salts with acids and bases with the proviso that when the A and B rings are

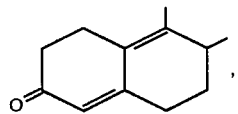

$R_1$ is

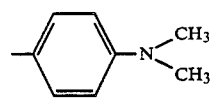

$R_2$ is methyl, $R_3$ is —OH, $R_4$ is phenyl having anti proliferative properties.

15 Claims, No Drawings

NOVEL 17-ARYL-STEROIDS

OBJECTS OF THE INVENTION

It is an object of the invention to provide the novel 17-aryl steroids of formula I and their pharmaceutically acceptable salts and a novel process and novel intermediates to prepare the same.

It is a further object of the invention to provide antiproliferative compositions and a novel pharmacological method of treating warm-blooded animals.

These and other objects and advantages of the invention will become obvious from the following detailed description.

THE INVENTION

The novel compounds of the invention are selected from the group consisting of compounds of the formula

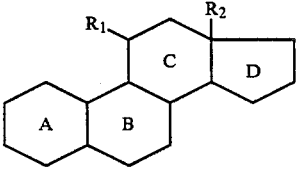

wherein $R_1$ is an organo of 1 to 18 carbon atoms optionally containing at least one heteroatom connected to the C ring by a carbon atom, $R_2$ is methyl or ethyl, the A and B rings are selected from the group consisting of (a) 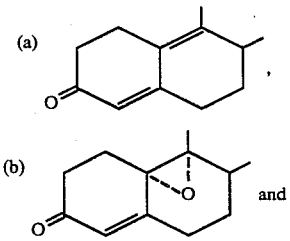

(b)

(c)

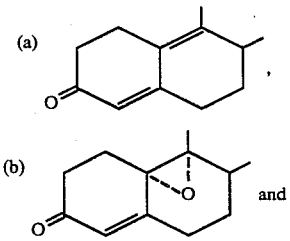

Re is selected from the group consisting of hydrogen, optionally substituted alkyl of 1 to 6 carbon atoms and acyl and the D ring is selected from the group consisting of

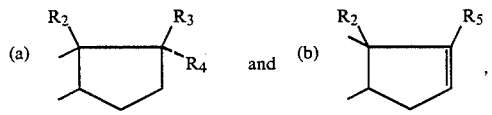

one of $R_3$ and $R_4$ is selected from the group consisting of hydroxy, protected hydroxy, acyl and alkoxy and the other is an optionally substituted aryl, $R_5$ is an optionally substituted aryl and their non-toxic, pharmaceutically acceptable salts with acids and bases with the proviso that when the A and B ring are

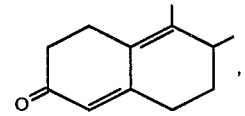

$R_1$ is

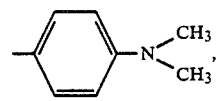

$R_2$ is methyl, $R_3$ is —OH and $R_4$ is phenyl.

Among the preferred compounds of formula I are those wherein D is

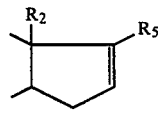

and A and B are

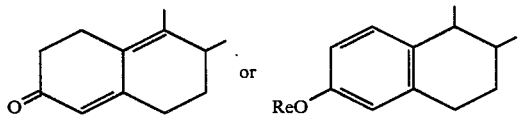

and $R_1$ is optionally unsaturated alkyl of 1 to 12 carbon atoms.

Examples of $R_1$ are methyl, ethyl, propyl, isopropyl, butyl, isobutyl, tert.-butyl, n-pentyl, n-hexyl, 2-methylpentyl, 2,3-dimethyl-butyl, n-heptyl, 2-methyl-hexyl 2,2-dimethyl-pentyl, 3,3-dimethyl-pentyl, 3-ethyl-pentyl, n-octyl, 2,2-dimethyl-hexyl, 3,3-dimethyl-hexyl, 3-methyl-3-ethyl-pentyl, nonyl, 2,4-dimethyl-heptyl, n-decyl; alkenyl such as vinyl, isopropenyl, allyl, 2-methyl-allyl or isobutenyl.

The said groups may be substituted with groups such as thioalkyl like thiomethyl or thioethyl; with at least one halogen such as fluorine, chlorine, bromine or iodine; amino substituents such as dimethylamino; aryl or aralkyl such as phenyl or benzyl which aryl may be substituted with at least one alkyl of 1 to 4 carbon atoms; alkoxy of 1 to 4 carbon atoms such as methoxy, ethoxy, isopropoxy, n-propoxy, butyloxy, isobutyloxy or tert.-butyloxy; alkenyloxy such as vinyloxy or allyloxy; halogens especially fluorine or chlorine; at least one member of the group consisting of —OH, —CF$_3$, alkylthio of 1 to 4 carbon atoms optionally oxidized to sulfoxide or sulfonic such as methylthio or ethylthio; acyl such as acetyl or propionyl preferably in the p-position; as well as aryl and aralkyl with different substituents such as 3-fluoro-4-dimethylamino-phenyl.

$R_1$ may also be a heterocycle optionally substituted with the above substitutents and specific heterocycles are thienyl, furyl, isothienyl, isofuryl, thiazolyl, isothiazolyl, oxazolyl, isoxazolyl, thiadiazolyl, pyridinyl or piperidinyl and other known heterocycles.

$R_1$ may also be cycloalkyl such as cyclopropyl, cyclobutyl, cyclopentyl or cyclohexyl or cycloalkenyl such as cyclobutenyl or cyclopentenyl; or a group having a substituted aryl or amino optionally substituted with one or two alkyl of 1 to 8 carbon atoms or an amino incorporated in a heterocycle optionally containing another heteroatom of oxygen, nitrogen or sulfur such as morpholino or piperidinyl.

The aryl is preferably phenyl and the aryl ring may be substituted with a substituted amino alkyl such as dimethylaminomethyl or dimethylaminoethyl or a substituted aminoalkoxy such as dimethylaminoethoxy, as well as a silica group such as trimethylsilyl-phenyl. The group containing a nitrogen atom can also be oxidized.

When the compounds have a $R_1$ containing a heteroatom, it is preferably nitrogen or sulfur. Among the preferred alkyls are methyl, ethyl, propyl, isopropyl, butyl, sec.-butyl, tert.-butyl, pentyl, hexyl, 2-methyl-pentyl and 2,2-dimethyl-pentyl.

When Re is substituted, it is preferably amino or dialkylamino such as dimethylamino. Examples of acyl are acetyl, propionyl, butyryl or benzoyl.

"Optionally protected hydroxy" means a hydroxy protected by the classic protective groups such as acyl like acetyl, chloroacetyl or trifluoroacetyl, tetrahydropyranyl, silyl groups such as trimethylsilyl or tert.butyl dimethylsilyl.

The term "optionally acylated hydroxy" means an hydroxy acylated with an acyl group such as acetyl. Examples of alkoxy are methoxy, ethoxy, propoxy, isopropoxy and butoxy.

Aryl includes carbocyclics and heterocyclics. Examples of 5-membered rings are thienyl, furyl, thiazolyl, pyrrolyl, oxazolyl, imidazolyl, pyrazolyl, triazolyl (1,2,3 or 1,2,4) tetrazolyl, isothiazolyl and isoxazolyl. Examples of 6-membered rings are phenyl, pyridinyl, pyridazinyl, pyrimidinyl and pyrazinyl.

Among the optional substituents for aryl are preferably halogens such as fluorine, chlorine, bromine or iodine; alkyl such as methyl, ethyl, propyl, isopropyl, butyl, isobutyl and tert.-butyl; alkoxy such as methoxy, ethoxy, propoxy, isopropoxy and butoxy; alkylthio such as methylthio, ethylthio, propylthio, isopropylthio, and butylthio; amino and mono and dialkylamino such as methylamino, ethylamino, dimethylamino, diethylamino or methylethylamino and oxidized dialkylamino; aminoalkyl such as aminomethyl or aminoethyl; dialkylaminoalkyl such as dimethylaminomethyl or dimethylaminoethyl; dialkylaminoalkoxy such as dimethylaminoethoxy; optionally acylated hydroxy such as acetoxy or

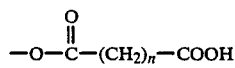

wherein n is 2 to 5 such as acetyl, propionyl, butyryl or benzoyl; free carboxy or esterified such as alkoxycarbonyl like methoxycarbonyl or ethoxycarbonyl; cyano; trifluoromethyl; aryl such as phenyl, furyl, thienyl or aralkyl such as benzyl with optional substituents such as alkyl, alkylthio, alkoxy, aminoalkyl or dialkylamino as discussed above.

The term "optionally substituted" means one or more identical or different substituents. The substituents may also be the above when $R_1$ is a substituted aryl.

Depending upon what substituents $R_1$, $R_3$, $R_4$ or $R_5$ are, it is possible to form pharmaceutically acceptable, non-toxic salts with bases and acids When one of the said Rs is a salifiable amino, it can form acid addition salts with acids such as hydrochloric acid, hydrobromic acid, nitric acid, sulfuric acid, phosphoric acid, acetic acid, propionic acid, formic acid, maleic acid, fumaric acid, succinic acid, tartaric acid, citric acid, oxalic acid, glyoxylic acid, aspartic acid, alkane sulfonic acids such as methane sulfonic acid or ethane sulfonic acid, aryl sulfonic acids such as benzene sulfonic acid or p-toluene sulfonic acid and aryl carboxylic acids such as benzoic acid.

When one of $R_1$, $R_3$, $R_4$, or $R_5$ contains a carboxy group, it may be salified with a base such as salts of sodium, potassium, lithium, calcium, magnesium or ammonia or with organic amines such as methylamine, propylamine, trimethylamine, diethylamine, triethylamine, N,N-dimethyl-ethanolamine, tris (hydroxy methyl) amino methane, ethanolamine, pyridine, picoline, dicyclohexylamine, morpholine, benzylamine, procaine, lysine, arginine, histidine or N-methyl-glucamine.

Among the preferred compounds of the invention of formula I are those wherein $R_1$ is optionally substituted aryl, especially optionally substituted phenyl with the preferred substituents being dimethylamino, methylthio, methoxy, acetyl and propionyl, preferably in the p-position.

Other preferred compounds of formula I are those wherein the A and B ring are

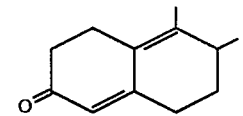

those wherein $R_3$ is hydroxy or methoxy and those wherein $R_4$ and $R_5$ are optionally substituted aryl, especially phenyl optionally substituted with methylthio, methoxy, dimethylamino, hydroxy or methyl.

Specific preferred compounds of formula I are 11β, 17α-bis-(4-dimethylamino-phenyl)-Δ$^{4,9}$-estradiene-17β-ol-3-one and 11β-(4-dimethylamino-phenyl)-17α-(3-methoxy-phenyl)-Δ$^{4,9}$-estradiene-17β-ol-3-one.

The novel process of the invention for the preparation of compounds of formula I comprises either (a) reacting a compound of the formula

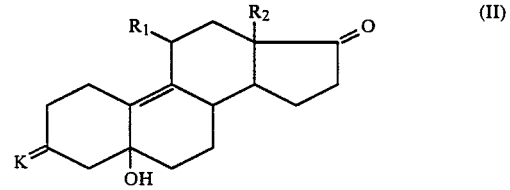

wherein $R_1$ and $R_2$ have the above definitions and K is a ketone protective group with (i) an organometallic derivative of an optionally substituted aryl of $R_3$ or $R_4$, (ii) optionally separating the isomers or effecting a deshydration in the 16(17)-position, (iii) then optionally in any order reacting with a protective agent, alkylation agent or acylation agent for a hydroxy in $R_3$ or $R_4$ and necessarily to a deshydration agent capable of freeing the ketone group to obtain compounds of the formula

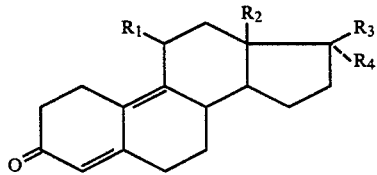

IA and

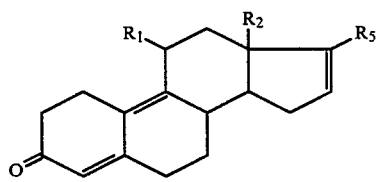

I'A wherein $R_1$, $R_2$, $R_3$, $R_4$ and $R_5$ have the above definitions and if desired reacting the latter with an oxidation reactant to obtain compounds of the formula

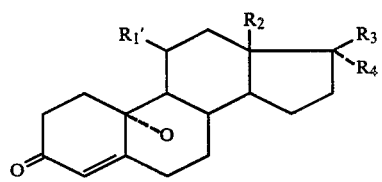

IB and

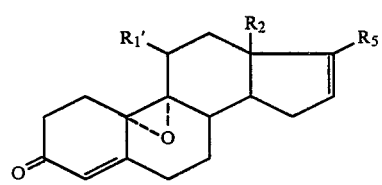

I'B wherein $R_2$, $R_3$, $R_4$ and $R_5$ have the above definitions and $R_1'$ is $R_1$ with any nitrogen atom oxidized and if desired treating the latter with a reducing agent to obtain the nitrogen atom in non-oxidized form or treating the compounds of formulae $I_A$ and $I_A'$ with an aromatization agent and optionally with an alkylation agent or acylation agent to obtain compounds of the formula

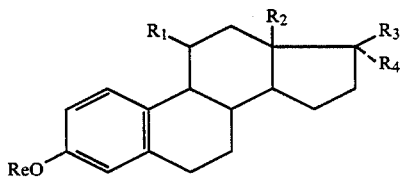

IC and

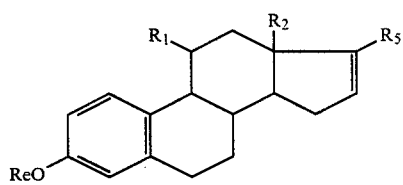

I'C wherein Re, $R_1$, $R_2$, $R_3$, $R_4$ and $R_5$ have the above definitions or (b) reacting a compound of the formula

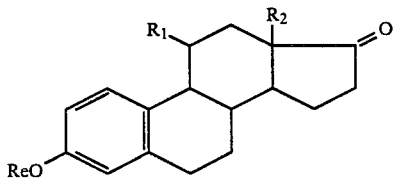

III wherein Re, $R_1$ and $R_2$ have the above definitions with an organometallic reactive derivative of an optionally substituted aryl of $R_3$ or $R_4$ and optionally in any order separating the isomers formed and optionally reacting the latter with a protective agent, alkylating agent or acylating agent of the hydroxy of $R_3$ or $R_4$ or a deshydration reaction in the 16(17)-position and if desired reacting the compounds of formulae $I_A$, $I_A'$, $I_B$, $I_B'$, IC and $I_C'$ with a base or acid to form these salts.

The ketone blocking group of K may be a cyclic ketal or non-cyclic ketal or thioacetal or oxime or methyloxime.

The organo metallic derivative of the optionally substituted aryl of $R_3$ or $R_4$ is preferably a magnesium derivative of the formula ArMgHal or a lithium derivative of the formula ArLi wherein Hal is halogen and Ar is an optionally substituted aryl. Preferably, Hal is chlorine, bromine or iodine and most preferably bromine and the reaction is effected in the presence of cerium chloride with reaction with the magnesium or lithium being introduced into the compounds of formulae II or III. The reaction medium is subjected to a strong acid such as hydrochloric acid, sulfuric acid or nitric acid.

Generally this steps results in the formation of a mixture of products with a group of the formula

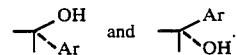

If it is preferred to produce predominantly or solely compounds with the group

which are compounds of the formula

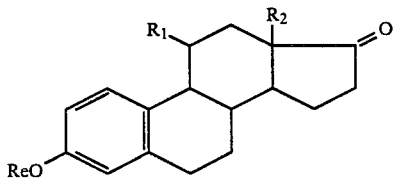

II' wherein $R_3'$ is —OH and $R_4'$ is optionally substituted aryl, the mixture of products formed by reaction with the magnesium derivative is subjected to known separation methods such as crystallization and preferably chromatography.

The deshydration reaction in the 16(17) position changes compounds of the formula

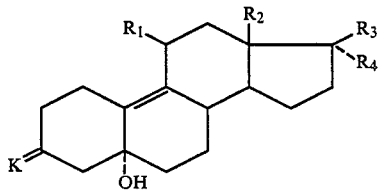

into the compounds of the formula

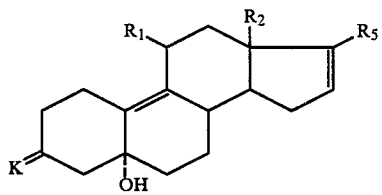

This reaction is very easily effected in certain cases, for example when the said deshydration reaction can be interposed before the chromatography to separate the 17-isomers.

In a preferred mode, the deshydration agent capable of liberating the ketone is a sulfonic acid resin in the acid form such as a commercial sulfonic acid resin on a polystyrene support or a styrene-divinyl benzene polymer support. Equally useful is a mineral acid such as hydrochloric acid or sulfuric acid in a lower alkanol or perchloric acid in acetic acid or a sulfonic acid such as p-toluene sulfonic acid or acetic acid.

The optional protection of the hydroxy group is effected by known methods using a derivative of the protective group such as a halide like trimethylsilyl chloride. The alkylation can also be effected by known methods such as reaction with an alkyl halide or alkyl sulfate such as alkyl iodide or methyl sulfate. The halide is preferred.

The optional acylation is also effected by classical methods such as reaction with an acyl halide such as acetyl chloride or a mixed or symmetrical anhydride such as acetic anhydride. The total or partial deshydration in the 16(17)-position equally causes a deshydration in the 4(5)-position capable of freeing the ketone group in the compounds of formula $II_A$.

The oxidation agent to transform the products of $I_A$ and $I_A{}'$ into compounds of formula $I_B$ and $I_B{}'$ respectively is preferably a peracid such as metachloro-perbenzoic acid, peracetic acid or perphthalic acid. When it is desired to obtain a compound in which the nitrogen atom of $R_1$ is oxidized, an equivalent of oxidation agent is used. When it is desired to form a compound in which B and C form an epoxide, two equivalents of the oxidation agent are used.

The reducing agent for the selective reduction of the N-oxide function is preferably triphenylphosphine in the presence of acetic acid for example. The aromatization agent to form the compounds of formulae $I_A$ and $I_A{}'$ into compounds of formulae $I_B$ and $I_B{}'$ may be selected from the group consisting of (a) palladium hydroxide deposited on magnesium in a lower alkanol such as methanol, (b) an acyl halide such as acetyl bromide optionally mixed with an acid anhydride such as acetic anhydride in a solvent such as methylene chloride for example followed by treatment with a base such as sodium hydroxide, potassium hydroxide or potassium bicarbonate.

The alkylation and acylation of the products of formulae $I_C$ or $I_C{}'$ is effected in a known manner. For example, alkylation may be effected with an alkyl halide or alkyl sulfate preferably alkyl iodide.

The reaction of a compound of formula III with the organo metallic compound, the separation and reaction of the resulting isomers, protective action, alkylation or acylation of the hydroxy effected with the product of formula I obtained starting from the products of formula III as well as the subsequent deshydration are effected under the indicated conditions. The optional formation of the salts with bases and acids is effected in the usual manner.

Therefore, for example, when the optional reactions of protection, alkylation or acylation of the hydroxy of $R_3$ or $R_4$ is to be effected for the compounds of formulae $I_B$ or $I_C$, then $R_3$ or $R_4$ is hydroxy in the formula.

The reaction of the organometallic compound with the products of formula III leads directly to the compounds of formula $I_C$. With these products, it is evident that one can optionally effect in any order a separation of the isomers and/or a reaction of protection or alkylation or acylation of the hydroxy of $R_3$ or $R_4$. Alternatively, the products of formula $I_C$ can be deshydrated in the 16(17)-position to obtain the corresponding compounds of formula $I_{C'}$.

The novel antiproliferative compositions of the invention are comprised of an antiproliferatively effective amount of at least one compound of formula I and its non-toxic, pharmaceutically acceptable salts and a pharmaceutical carrier or excipient. The compositions may be in the form of tablets, dragees, gelules, granules, suppositories, ovules, injectable solutions or suspensions, pommades, creams and gels.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants, or emulsifiers and preservatives.

Contrary to the products of formula I wherein the A and B rings are

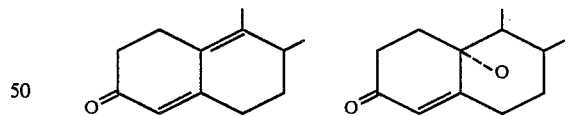

which are practically devoid of estrogenic and/or antiestrogenic activities, the compounds of formula I in which the A and B rings are

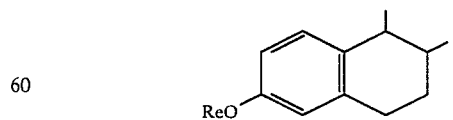

present estrogenic and/or antiestrogenic properties.

These properties make these compounds of formula I useful in the treatment of hormono-dependent carcinomas such as mammary carcinomas and their metastases as well as in the treatment of benign tumors of the breast. The estrogenic and/or antiestrogenic properties of these compounds also makes them useful for the treatment of troubles attached to a hypofolliculinia such as amenorrhees, dysmenorrhees, repeated abortions, premenstrual troubles and the treatment of menopause.

The compounds of formula I also possess progestomimetic activity, principally antiprogestomimetic activity as well as glucocorticoidal and/or antiglucocorticoidal activity as shown by the affinity for exposed receptors. The antiprogestomimetic activity of the compounds of formula I make them useful as contraceptives or abortives as well as hormone deregulators.

Some of the compounds of formula I and their salts also have progestomimetic properties and are used in the treatment of amenorrhees, dysmenorrhees and luteal insufficiencies.

The compounds of formula I and their salts which possess antiglucocorticoidal properties are useful principally to combat against the secondary effects of glucocorticoids, to combat the troubles due to a hypersecretion of glucocortiocids and especially against aging in general and more particularly against hypertension, atherosclerosis, osteoporosis, diabetes, obseity as well as immunodepression and insominia.

The novel method of the invention of inducing antiproliferative activity in warm-blooded animals comprises administering to warm-blooded animals an antiproliferatively effective amount of at least one compound of formula I and their non-toxic, pharmaceutically acceptable acid addition salts. The compounds may be administered reactally, orally, parenterally or topically. The usual daily dose is 0.013 to 13.3 mg/kg depending on the condition treated, the specific compound and the method of administration. The preferred oral dose is 0.013 to 1.3 mg/kg per day.

The starting compounds of formula I are known or can be made by known methods such as described in European patent No. 0,057,115 or by Step A of Examples 1 to 17 infra.

The compounds of formula III may be prepared starting from the compounds of formula II as described in Steps A and B of Example 14. Generally, the compounds of formula II are subjected to a deshydration reaction capable of freeing the ketone under the indicated conditions and the resulting compounds of the formula

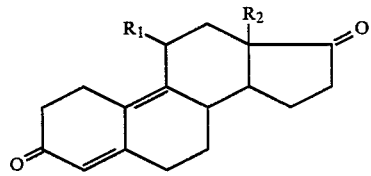

III' are treated either with an oxidation agent to obtain a compound of the formula

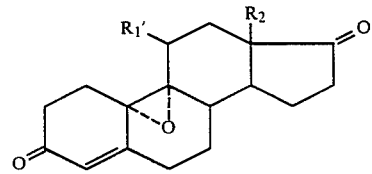

III"

wherein $R_1$ and $R_2$ have the above definitions and then optionally with a reducing agent to obtain a compound of formula III" in which $R_1$ contains an non-oxidized nitrogen atom or with an aromatization agent and then optionally with an alkylation agent or an acylation agent to obtain a compound of the formula

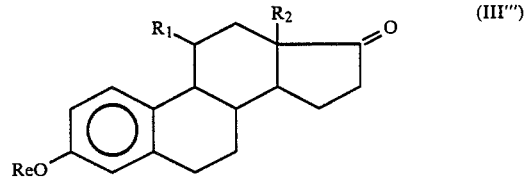

(III''')

The novel intermediates of the invention are the compounds of formula III and among the preferred compounds are those wherein $R_1$ is aryl, especially optionally substituted phenyl.

In addition to the specific compounds of the working examples, other compounds of formula I includes compounds of the formula.

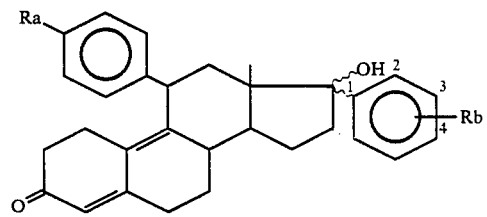

| Ra | Rb |
|---|---|
| COCH$_3$ | 4-N(CH$_3$)$_2$ |
| N—(CH$_3$)$_2$ | 4-COCH$_3$ |
| SCH$_3$ | 4-SCH$_3$ |
| SCH$_3$ | 3SCH$_3$ |
| N—(CH$_3$)$_2$ ↓ O | N—(CH$_3$)$_2$ ↓ O |
| (CH$_3$)$_2$N—(CH$_2$)$_2$—O— | 3-OH |
| (CH$_3$)$_2$N—(CH$_2$)$_2$—O— | 4-N(CH$_3$)$_2$ |

(2) of the formula

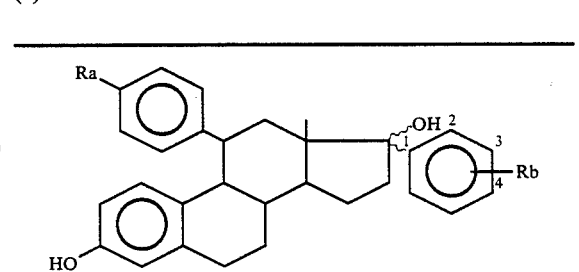

| Ra | Rb |
|---|---|
| N—(CH$_3$)$_2$ | 3-OH |
| (CH$_3$)$_2$N—(CH$_2$)$_2$—O— | 3-OH |
| (CH$_3$)$_2$N—(CH$_2$)$_2$—O— | 4-N(CH$_3$)$_2$. |

The wavy line indicates that the —OH and

have 2 possible configurations and preferably the —OH is in the β-position and the aryl is in the α-position.

(3) of the formula

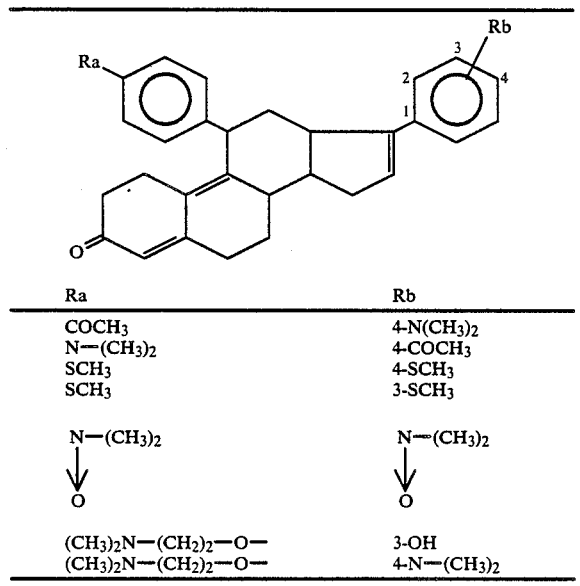

| Ra | Rb |
|---|---|
| COCH₃ | 4-N(CH₃)₂ |
| N—(CH₃)₂ | 4-COCH₃ |
| SCH₃ | 4-SCH₃ |
| SCH₃ | 3-SCH₃ |
| N—(CH₃)₂ ↓ O | N—(CH₃)₂ ↓ O |
| (CH₃)₂N—(CH₂)₂—O— | 3-OH |
| (CH₃)₂N—(CH₂)₂—O— | 4-N—(CH₃)₂ |

(4) Products of the formula

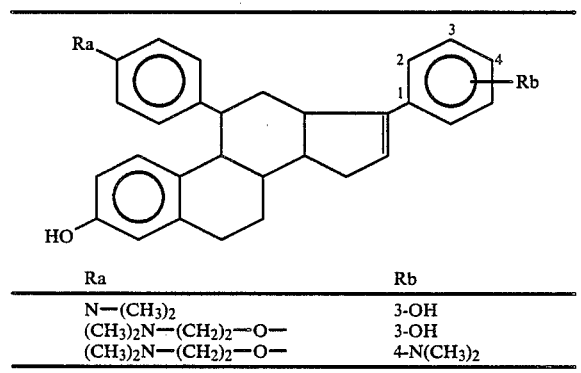

| Ra | Rb |
|---|---|
| N—(CH₃)₂ | 3-OH |
| (CH₃)₂N—(CH₂)₂—O— | 3-OH |
| (CH₃)₂N—(CH₂)₂—O— | 4-N(CH₃)₂ |

In the following examples there are described several preferred embodiments to illustrate the invention. However, it is to be understood that the invention is not intended to be limited to the specific embodiments.

EXAMPLE 1

11β,17α-bis-(4-methoxy-phenyl)-Δ⁴,⁹-estradiene-17β-ol-3-one

Step A: 3,3-(1,2-ethanediyl)-cyclic acetal of 11β-(4-methoxy-phenyl)-Δ⁹-estrene-5α-ol-3,17-dione 78 ml of a solution of 0.77M 4-methoxy phenyl magnesium bromide in tetrahydrofuran were cooled to −20° C. and then 600 mg of anhydrous cuprous chloride were added. The mixture was stirred for 15 minutes and then a solution of 6.6 g of 3,3-(1,2-ethanediyl)-cyclic acetal of 5α,10α-epoxy-Δ⁹⁽¹¹⁾-estrene-3,17-dione in 66 ml of anhydrous tetrahydrofuran was added over 30 minutes at −20° C. The mixture stood for one hour at −20° C. and was then poured into 400 ml of a solution of ammonium chloride and ice. The mixture was extracted with ethyl acetate and the organic phase was washed with aqueous sodium chloride, dried and evaporated to dryness. The residue was taken up in 20 ml of boiling ethyl acetate and the solution was cooled to 0°–5° C. and vacuum filtered to obtain 5.5 g of product. The latter was dissolved in 100 ml of boiling methylene chloride and isopropyl ether was added to the solution to obtain 4.84 g of 3,3-(1,2-ethanediyl)-cyclic acetal of 11-(4-methoxy-phenyl)Δ⁹-estrene-5α-ol-3,17-dione. The crystallization mother liquors were evaporated to dryness and the residue was chromatographed over silica. Elution with a 6-4 mixture of cyclohexane and ethyl acetate yielded 1.9 g of the expected compound melting at 130° C. and 1.85 g of the corresponding 17-keto compound.

IR Spectrum (CHCl₃): OH: 3510 cm⁻¹ of 5—OH; C=O: 1732 cm¹ and 4-methoxy phenyl: 1608 cm⁻¹, 1580 cm⁻¹, 1510 cm⁻¹.

STEP B:

11β,17α-bis-(4-methoxy-phenyl)-Δ⁴,⁹-estradiene-17β-ol-3-one 0.5 ml of 2N hydrochloric acid were added to a solution of 547 mg of the product of Step A in 20 ml of methanol and the mixture was stirred at room temperature for one hour. 100 ml of water were added to the mixture which was then vacuum filtered. The product was dried at 60° C. under reduced pressure and the 246 mg of product were chromatographed over silica. Elution with a 6-4 cyclohexane-ethyl acetate mixture yielded 360 mg of 11β, 16α-bis-(4-methoxy-phenyl)-Δ⁴,⁹-estradiene-17β-ol-3-one melting at 260° C. The product was taken up in 8 ml of methylene chloride and isopropyl ether was added. The mixture was concentrated and vacuum filtered to obtain 330 mg of the product melting at 260° C.

IR Spectrum (CHCl₃): C=O: 1645 cm⁻¹-1655 cm⁻¹; OH: 3600 cm⁻¹. aromatic+conjugated C=C: 1608 cm⁻¹, 1600 cm⁻¹, 1581 cm⁻¹ 1510 cm⁻¹.

EXAMPLE 2

11β,17α-bis-(4-dimethylamino-phenyl)-Δ⁴,⁹-estradiene-17β-ol-3-one

STEP A: (1,2-ethanediyl) cyclic acetal of 11β,17α-bis-(4-dimethylamino-phenyl)-Δ⁹-estrene-5α,17β-diol-3-one (product A) and (1,2-ethanediyl) cyclic acetal of 11α, 17-bis-(4-dimethylamino-phenyl)-Δ⁹,¹⁶-estradiene-5α-ol-3-one (product B)

3.7 g of cerium chloride were dried for 2 hours at 140° C. under reduced pressure and then were cooled under an inert anhydrous atmosphere. 30 ml of tetrahydrofuran were added thereto and the mixture was stirred at room temperature for two hours. After cooling to 0° C., 25 ml of a solution of 0.77M of 4-dimethylamino-phenyl magnesium bromide in tetrahydrofuran were added and the mixture was stirred at 0° C. for one hour. At solution of 2.26 g of 3,3-(1,2-ethanediyl) cyclic acetal of 11β-(4-dimethylamino-phenyl)-Δ⁴,⁹-estradiene-5α-ol-3,17-dione in 15 ml of anhydrous tetrahydrofuran was added and the mixture was allowed to return to room temperature. After one and a half hours, the mixture was poured into aqueous ammonium chloride and the mixture was washed with ethyl acetate, stirred and filtered. The filtrate was extracted with ethyl acetate and the organic phase was washed with water, dried and evaporated to dryness. The residue was chromatographed over silica and eluted with an 8-2 methylene chloride-ethyl acetate mixture to obtain after crystallization from ether 975 mg of product A melting at 262° C. The rest of the chromatography fractions and and the crystallization mother liquors were combined and chromatographed again to obtain 470 mg of product A and 655 mg of product B melting at 214°-216° C.

STEP B:

11β,17α-bis-(4-dimethylamino-phenyl)-Δ$^{4,9}$-estradiene-17-β-ol-3-one

A solution of 865 mg of product A of Step A in 8 ml of methanol and 4 ml of 2N hydrochloric acid stood at room temperature for one hour and was then made alkaline by stirring while adding aqueous sodium bicarbonate solution. The mixture was extracted with methylene chloride and the organic phase was washed with water, dried and evaporated to dryness to obtain 835 mg of raw product. The latter was crystallized from ether and then ether and methylene chloride to obtain the expected product melting at 232° C.

IR Spectrum (CHCl$_3$): free OH: 3600 cm$^{-1}$; 3-keto; 1653 cm$^{-1}$; aromatic bonds: 1560 cm$^{-1}$, 1518 cm$^{-1}$, 1612 cm$^{-1}$.

EXAMPLE 3

11β,17-bis-(4-dimethylamino-phenyl)-Δ$^{4,9,16}$-estratriene-3-one

A solutionn of 540 mg of product B of Step A of Example 2, 8 ml of methanol and 4 ml of 2N hydrochloric acid stood for one hour at room temperature and was then made alkaline with an aqueous sodium bicarbonate solution. The mixture was extracted with methylene chloride and the organic phase was washed with water, dried and evaporated to dryness. The residue was chromatographed over silica and eluted with a 9-1 methylene chloride-ethyl acetate mixture to obtain 400 mg of the expected product.

IR Spectrum (CHCl$_3$): dienone: 1653 cm$^{-1}$, 1600 cm$^{-1}$, 863 cm$^{-1}$; 4-dimethylaminophenyl; 1611 cm$^{-1}$ and 1518 cm$^{-1}$.

EXAMPLE 4

11β-(4-dimethylamino-phenyl)-17α-(4-methoxy-phenyl)-Δ$^{4,9}$-estradiene-17β-ol-3-one STEP A: (1,2-ethanediyl)-cyclic acetal of 11β-(4-dimethylaminophenyl)-17α-(4-methoxy-phenyl)-Δ$^9$-estrene-17β-ol-3-one (product A) and its 17β-(4-methoxy-phenyl)-isomer (product B)

Using the procedure of Step A of Example 2, 12 ml of a solution of 0.9M of 4-methoxy-phenyl magnesium bromide in tetrahydrofuran were reacted and the extraction residue was chromatographed over silica. Elution with an 8-2 cyclohexane-ethyl acetate mixture yielded 980 mg of product A which melted at 209° C. after crystallization from a methylene chloride-isopropyl ether and 609 mg of product B which melted at 264° C. after crystallization from methanol.

STEP B:

11β-(4-dimethylamino-phenyl)-17α-(4-methoxy-phenyl)-Δ$^{4,9}$-estradiene-17β-ol-3-one 5 ml of 2N hydrochloric acid were added to a solution of 1.54 g of product A of Step A in 35 ml of methanol and after standing for 90 minutes, the mixture was poured into aqueous sodiumm bicarbonate. The mixture was extracted with ethyl acetate and the organic phase was washed with water, dried and evaporated to dryness. The residue was chromatographed over silica and eluted with a 9-1 methylene chloride-ethyl acetate mixture to obtain 1.38 g of the expected product melting at 266° C. after crystallization from an ether-isopropyl ether mixture.

IR Spectrum (CHCl$_3$): OH: 3600 cm$^{-1}$; C═O: 165 cm$^{-1}$; aromatic bonds: 1611 cm$^{-1}$, 1560 cm$^{-1}$, 1517 cm$^{-1}$.

EXAMPLE 5

11β-(4-dimethylamino-phenyl)-17-(4-methoxy-phenyl)-Δ$^{4,9,16}$-estratriene-3-one A solution of 680 mg of product B of Example 4, 20 ml of methanol and 2.5 ml of 2N hydrochloric acid stood at room temperature for 90 minutes and was then diluted with water and made alkaline by addition of aqueous sodium bicarbonate. The mixture was extracted with methylene chloride and the organic phase was washed with water, dried and evaporated to dryness to obtain a mixture of the desired product and its 17α-methoxy-17β-4-methoxy-phenyl derivative. The residue was dissolved in 4 ml of tetrahydrofuran and 2 ml of 2N hydrochloric acid and the solution stood for 3 hours, was washed with water, then with aqueous sodium bicarbonate. The mixture was extracted with methylene chloride and the organic phase was washed with water and dried to obtain 603 mg of the desired product with a specific rotation of $[\alpha]_D = +247°$ (c=1% in CHCl$_3$).

IR Spectrum (CHCl$_3$): 3 C═O: 1654 cm$^{-1}$; aromatic bonds; 1611 cm$^{-1}$, 1569 cm$^{-1}$, 1517 cm$^{-1}$ and 1510 cm$^{-1}$.

EXAMPLE 6

11β-(4-dimethylamino-phenyl)-17α-(4-hydroxy-phenyl)-Δ$^{4,9}$-estradiene-17β-ol-3-one (product A) and 11β-(4-dimethylaminophenyl)-17-(4-hydroxy-phenyl)-Δ$^{4,9,16}$-estratriene-3-one (product B)

Using the procedure of Step A of Example 2, 20 ml of a solution of 0.72M of 4-(2'-tetrahydropyranyloxy)-phenyl magnesium bromide in tetrahydrofuran were reacted and the mixture was poured into an iced solution of 100 ml of water and 5 ml of acetic acid. The mixture was extracted with ethyl acetate and the organic phase was washed with aqueous sodium bicarbonate and then with water, dried and evaporated to dryness. The residue was dissolved in 20 ml of methanol and after the addition of 5 ml of 2N hydrochloric acid, the mixture was stirred for 90 minutes and poured into an aqueous sodium bicarbonate solution. The mixture was extracted with methylene chloride and the organic phase was evaporated to dryness. The residue was chromatographed over silica and eluted with an 8-2 methylene chloride-ethyl acetate mixture to obtain 720 mg of product B and 730 mg of product A. Product B was again chromatographed over silica and was eluted with a 7-3 benzene-ethyl acetate mixture to obtain 495 mg of product B with a specific rotation of $[\alpha]_D = +240° \pm 3°$ (c=1% in CHCl$_3$).

Product A was chromatographed again over silica and eluted with a 6-4 benzene-ethyl acetate mixture to obtain 540 mg of product A which was crystallized from ethyl acetate and then isopropanol to obtain 463 mg of solvated product A melting at ≃208° C. and having a specific rotation of $[\alpha]_D = +133°$ (c=1% in CHCl$_3$).

IR Spectrum (CHCl₃): OH: 3596 cm⁻¹ and associated; 3-keto: 1651 cm⁻¹; aromatic: 1621 cm⁻¹, 1594 cm⁻¹, 1562 cm⁻¹.

EXAMPLE 7

17α-(4-dimethylamino-phenyl)-11β-(4-methylthio-phenyl)-Δ⁻⁹-estrene-17βol-3-one STEP A: 3,3-(1,2-ethendiyl)-cyclic acetal of 11β-(4-methylthiophenyl)-Δ⁹⁽¹¹⁾-estrene-5α-ol-3,17-dione 100 ml of a solution of 0.75M of 4-(methylthiophenyl)magnesium bromide in tetrahydrofuran were added dropwise over 75 minutes at −6° C. to a mixture of 0.672 g of cuprous chloride, 0.212 g of lithium chloride, 165 ml of tetrahydrofuran and 16.5 g of 3,3-(1,2-ethanediyl)-cyclic acetal of 5α,10α-epoxy-Δ⁹,⁽¹¹⁾-estrene-17-one and the mixture was stirred under an inert atmosphere at −10 C. for one hour. 100 ml of an aqueous saturated ammonium chloride solution were added and after stirring for 10 minutes, the mixture was extracted with ethyl acetate. The organic phase was washed with water, dried and evaporated to dryness under reduced pressure and the residue was taken up in hexane and filtered. The crystallized product was washed with hexane and dried to obtain 22.2 g of raw product melting at 202° C. 2 g of the product were chromatographed on silica and eluted with a 1-1 mixture of cyclohexane-ethyl acetate containing 0.1% triethylamine and after crystallization from ethyl acetate, the 0.928 g of the expected product melted at 209 C.

STEP B: (1,2-ethanediyl)-cyclic acetal of 11β-(4-methylthio-phenyl)-17α-(4-dimethylamino-phenyl)-Δ⁹-estrene-5α,17β-diol-3-one (product A) and (1,2-ethanediyl)-cyclic acetal of 11β-(4-methylthio-phenyl)-17α-(4-dimethylamino-phenyl)-Δ⁹-estrene-5,17α-diol-3-one (product B).

7.7 g of cerium chloride were dehydrated at 150° C. and a pressure of 1 mm Hg for 2 hours and then 35 ml of a solution of 0.87M of 4-dimethylamino-phenyl magnesium bromide in tetrahydrofuran were added at 5° C. over 10 minutes. A solution of 5 g of the raw product of Step A melting at 202° C. in 40 ml of anhydrous tetrahydrofuran was added and the temperature was permitted to rise to room temperature. Another 12 ml of the magnesium solution were added and the mixture stood overnight at room temperature and was poured into 200 ml of aqueous 10% ammonium chloride solution. The decanted organic phase was washed with aqueous sodium chloride solution and the wash water was extracted with ethyl acetate. The combined organic phases were dried and evaporated to dryness and the residue was chromatographed over silica. Elution with a 7-3 methylene chloride-ethyl acetate mixture containing 1% triethylamine under pressure yielded 1.97 g of product A with a Rf=0.44 and 1.08 g of product B with a Rf=0.21.

IR Spectrum (CHCl₃) for A and B: 5-OH: 3510 cm⁻¹; 17-OH: 3598 cm⁻¹;

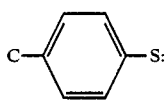

1491 cm⁻¹;

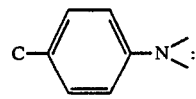

1611, 1559, 1520 cm⁻¹.

STEP C: 11β-(4-methylthio-phenyl)-17α-(4-dimethylamino-phenyl)-Δ⁴,⁹-estraidene-17β-ol-3-one 5 ml of 2N hydrochloric acid were added to a solution of 1.94 g of product A of Step B in 20 ml of tetrahydrofuran and after stirring for 50 minutes, the mixture was poured into an aqueous sodium bicarbonate solution. The mixture was extracted with ethyl acetate and the organic phase was washed with water, dried and evaporated to dryness. The residue was chromatographed over silica and eluted with an 8-2 methylene chloride-ethyl acetate mixture to obtain 1.24 g of product. The latter was dissolved in 10 ml of methylene chloride and hot isopropyl ether was added. The mixture was concentrated, iced and vacuum filtered to obtain 1.055 g of the expected compound melting at 236° C. and having a specific rotation of [α]_D= +75°±1.5° (c=1% in CHCl₃).

EXAMPLE 8

11β-(4-methylthio-phenyl)-17β-(4-dimethylamino-phenyl)-Δ⁴,⁹-estradiene-17α-ol-3-one (product A) and 11β-(4-methylthiophenyl)-17-(4-dimethylamino-phenyl)-Δ⁴,⁹,¹⁶-estratriene-3-one (product B)

5.4 ml of N hydrochloric acid were added to a solution of 1.03 g of the product of Step B of Example 7 in 10 ml of tetrahyrofuran and after stirring for 30 minutes, the mixture was poured into 20 ml of aqueous sodium bicarbonate solution. The mixture was extracted with ethyl acetate and the organic phase was washed with aqueous sodium chloride, dried and evaporated to dryness. The residue was chromatographed over silica and eluted with a 7-3 cyclohexane-ethyl acetate mixture containing 0.1% of triethylamine to obtain 470 mg of product B and 115 mg of product A. The latter was dissolved in 4 ml of methylene chloride and 10 ml of isopropyl ether were added and the solution was concentrated, iced and vacuum filtered to obtain 95 mg of product A melting at 222° C.

IR Spectrum (CHCl₃)-Product A: free OH: 3597 cm⁻¹; C=O: 1652 cm⁻¹;

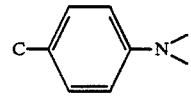

1613 cm⁻¹, 1558 cm⁻¹, 1521 cm⁻¹;

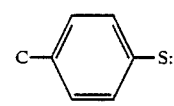

1492 cm⁻¹.

Product B had a specific rotation of [α]_D= +178.5°±2.5° (c=1% in CHCl₃).

EXAMPLE 9

11β-(4-dimethylamino-phenyl)-17α-(4-methyl-phenyl)-Δ$^{4,9}$-estradiene-17β-ol-3-one (product A) 11β-(4-dimethylamino-phenyl)-17β-(4-methyl-phenyl)-Δ$^{4,9}$-estradiene-17α-ol-3-one (product B) 11β-(4-dimethylamino-phenyl)-17α-methoxy-17β-(4-methyl-phenyl)-Δ$^{4,9}$-estradiene-3-one (product C)

STEP A: (1,2-ethanediyl)-cyclic acetal of 11β-(4-dimethylamino-phenyl)-17α-(4-methyl-phenyl)-Δ$^9$-estrene-5α,17β-diol-3-one and its 17β-(4-methyl-phenyl)isomer A mixture of 1.45 g of magnesium turnings and 2 ml of a solution of 8.5 g of p-bromo-toluene in 44 ml of anhydrous tetrahydrofuran was heated at 50° C. and reaction began. The mixture stood for one hour and was then stirred for 45 minutes at 50° C. to obtain a magnesium solution, titrating 0.89N. Using the procedure of Step A of Example 2, 18 ml of the magnesium solution were reacted and poured into an iced solution of aqueous 4% acetic acid solution. The mixture was extracted with ethyl acetate and the organic phase was washed with water, filtered and the insoluble was dried under reduced pressure to obtain 451 mg of 17β-(4-methyl-phenyl)-isomer melting at 305° C. Drying and evaporation of the filtrate yielded 1.8 g of a mixture of the 17α- and 17β-(4-methyl-phenyl)-isomers.

STEP B:
11β-(4-dimethylamino-phenyl)-17α-(4-methyl-phenyl)-Δ$^{4,9}$estradiene-17β-ol-3-one (product A)
11β-(4-dimethylamino-phenyl)-17β-(4-methyl-phenyl)Δ$^{4,9}$-estradiene-17α-ol-3-one (product B) and
11β-(4-dimethylamino-phenyl)-17α-methoxy-17β-(4-methylphenyl)-Δ$^{4,9}$-estradiene-3-one (product C)

A solution of 1.8 g of the mixture of Step A in 10 ml of 2N hydrochloric acid was stirred for 2 hours under an inert atmosphere and was then poured into aqueous sodium bicarbonate solution. The mixture was extracted with ethyl acetate and the organic phase was washed with aqueous saturated sodium chloride solution, dried and evaporated to dryness. The residue was chromatographed on silica and eluted with a 9-1 methylene chloride-ethyl acetate mixture to obtain 195 mg of product C and 672 mg of product A. Crystallization of product A from a methylene chloride-isopropyl ether yielded 550 mg of product A melting at 262 C. and having a specific rotation of $[\alpha]_D = 167° \pm 2.5°$ (c=1% in CHCl$_3$).

445 mg of the 17β-(4-methyl-phenyl)-isomer of Step A were dissolved in 5 ml of methanol and 1 ml 2N hydrochloric acid were added. After stirring at room temperature for one hour, the mixture was poured into aqueous sodium bicarbonate solution and was extracted with ethyl acetate. The organic phase was washed with water, dried and evaporated to dryness and the residue was chromatographed over silica. Elution with a 8-2 methylene chloride-ethyl acetate mixture yielded 130 mg of product C and 220 mg of product B. Product B was crystallized from a methylene chloride-isopropyl ether mixture and then a 1-1 methylene chloride-ethyl acetate mixture to obtain 146 mg of product B melting at 304° C.

195 mg and 130 mg of product C were crystallized from a methylene chloride-isopropyl ether mixture to obtain 227 mg of product C melting at 238° C. and having a specific rotation of $[\alpha]_D = +170° \pm 2.5°$ (c=1% in CHCl$_3$).

EXAMPLE 10

11β-(4-dimethylamino-phenyl)-17α-(2-hydroxy-phenyl)-Δ$^{4,9}$-estradiene-17β-ol-3-one (product A) and
11β-(4-dimethylamino-phenyl)-17β-(2-hydroxy-phenyl)-Δ$^{4,9}$-estradiene-17α-ol-3-one (product B)

STEP A: (1,2-ethanediyl)-cyclic acetal of 11β-(4-dimethylamino-phenyl)-17α-(2-hydroxy-phenyl)-Δ$^9$-estrene-5α,17β-diol-3-one and its 17β-(2-hydroxy-phenyl)-isomer Using the procedure of Example 9, 12.9 g of 2-bromophenyl tetrahydropyranyl ether was heated to 55° to 60° C. to obtain a magnesium solution titrating 0.67N. Using the procedure of Step A of Example 2, 40 ml of the said solution were heated to 40° C. for 5 hours and after extraction and evaporation of the solvent, the residue was chromatographed over silica and eluted with a 1-1 cyclohexane-ethyl acetate mixture to obtain 973 mg of the 17α-(2-hydroxy-phenyl)-isomer and 595 mg of a mixture of the 17α and 17β-isomers. The 973 mg of the 17β-isomer were crystallized from a methylene chloride-isopropyl mixture to obtain 758 mg of the expected isomer melting at 287° C.

STEP B:
11β-(4-dimethylamino-phenyl)-17α-(2-hydroxy-phenyl)-Δ$^{4,9}$-estradiene-17β-ol-3-one (product A) and
11β-(4-dimethylamino-phenyl)-17β-(2-hydroxy-phenyl)-Δ$^{4,9}$-estradiene-17α-ol-3-one (product B)

6.5 ml of N hydrochloric acid were added to a solution of 1.27 g of the 17α-isomer of Step A in 13 ml of tetrahydofuran and after standing at room temperature, the mixture was poured into aqueous sodium bicarbonate solution. The mixture was extracted with ethyl acetate and the organic phase was washed with water, dried and evaporated to dryness. The residue was chromatographed over silica and eluted with a 6-4 cyclohexaneethyl acetate mixture to obtain 847 mg of product A which was crystallized from a methylene chloride-ethyl acetate mixture to obtain 780 mg of product A melting at 266° C. and having a specific rotation of $[\alpha]_D = +185° \pm 2.5°$ (c=1% in CHCl$_3$).

170 mg of the mixture of Step A were dissolved in 2 ml of tetrahydrofuran and after adding 1.5 ml of N hydrochloric acid, the mixture stood for one hour and was poured into aqueous sodium bicarbonate solution. The mixture was extracted with ethyl acetate and the organic phase was washed with water, dried and evaporated to dryness. The residue was crystallized from a chloroform-isopropyl ether mixture and then a chloroformmethanol mixture to obtain 105 mg of product B melting at 275° C. and having a specific rotation of $[\alpha]_D = +112 \pm 2.5$ (c=0.46% in CHCl$_3$).

EXAMPLE 11

11β-(4-dimethylamino-phenyl)-17α-(2-methoxy-phenyl)-Δ$^{4,9}$-estradiene-17β-ol-3-one (product A) and 11β-(4-dimethylamino-phenyl)-17β-(2-methoxy-phenyl)-Δ$^{4,9}$-estradiene-17α-ol-3-one (product B)

STEP A: (1,2-ethanediyl)-cyclic acetal of 11β-(4-dimethylamino-phenyl)-17α-(2-methoxy-phenyl)-Δ$^9$-estrene-17β-ol-3-one and its 17β-(2-methoxy-phenyl)-isomer Using the procedure of Step A of Example 4, 25 ml of an 0.8N (2-methoxy-phenyl) magnesium bromide tetrahydrofuran solution were reacted and after chromatography on silica and elution with cyclohexane and then with a 6-4 ethyl acetate-cyclohexane mixture, 806 mg of the 17α-(2-methoxy-phenyl)-isomer and 1.44 g of the 17β-isomer were obtained. The 17α-isomer was crystallized from a methylene chloride-isopropyl ether mixture to obtain 738 mg of the product melting at 242°–244° C.

STEP B:

11β-(4-dimethylamino-phenyl)-17α-(2-methoxy-phenyl)-Δ$^{4,9}$-estradiene-17β-ol-3-one (product A) and 11β-(4-dimethylamino-phenyl)-17β-(2-methoxy-phenyl)-Δ$^{4,9}$-estradiene-17α-ol-3-one (product B).

3.15 ml of N hydrchloric acid were added to a solution of 588 mg of 17α-(2-methoxy-phenyl)-isomer of Step A in 8 ml of tetrahydrofuran and after standing at room temperature for 45 minutes, the mixture was poured into an aqueous sodium bicarbonate solution and was extracted with ethyl acetate. The organic phase was washed with water, dried and evaporated to dryness under reduced pressure. The residue was chromatographed on silica and eluted with a 4–6 cyclohexane-ethyl acetate mixture to obtain 390 mg of product A. The latter was dissolved in 20 ml of refluxing ethyl acetate and the solution was filtered, concentrated under reduced pressure, cooled and vacuum filtered to obtain 297 mg of product A melting at 264° C. and having a specific rotation of $[\alpha]_D = +198° \pm 3°$ (c=1% in CHCl$_3$).

Using the above procedure, 1.4 g of the 17β-(2-methoxyphenyl)-isomer of Step A were reacted and eluted with a 1—1 cyclohexane-ethyl acetate mixture to obtain 732 mg of product B which after crystallization from ethyl acetate melted at 222° C. and had a specific rotation of $[\alpha]_D = +163° \pm 2.5°$ (c=1% in CHCl$_3$).

EXAMPLE 12

11β-(4-dimethylamino-phenyl)-17α-(3-methoxy-phenyl)-Δ$^{4,9}$-estradiene-17β-ol-3-one (product A) and 11β-(4-dimethylaminophenyl)-17β-(3-methoxy-phenyl)-Δ$^{4,9}$-estradiene-17α-ol-3-one (product B)

STEP A: (1,2-ethanediyl)-cyclic acetal of 11β-(4-dimethylaminophenyl)-17α-(3-methoxy-phenyl)-Δ$^9$-estrene-5α,17β-diol-3-one and the (1,2-ethanediyl)-cyclic acetal of its 17β-(3-methoxyphenyl)-isomer Using the procedure of Example 11, 9.44 g of (3-methoxyphenyl)-magnesium bromide solution were reacted to obtain 600 mg of the 17α-(3-methoxy-phenyl)-isomer melting at 220° C. and 1.104 g of the 17β-(3-methoxy-phenyl)-isomer melting at 252° C.

STEP B:

11β-(4-dimethylamino-phenyl)-17α-(3-methoxy-phenyl)-Δ$^{4,9}$-estradiene-17β-ol-3-one (product A) and 11β-(4-dimethylamino-phenyl)-17β-(3-methoxy-phenyl)-Δ$^{4,9}$-estradiene-17α-ol-3-one (product B)

Using the procedure of Step B of Example 11, 594 mg of the 17α-(3-methoxy-phenyl) isomer of Step A were reacted to obtain 337 mg of product A with a specific rotation of $[\alpha]_D = +137° \pm 2°$ (c=0.9% in CHCl$_3$). Using the same procedure, 1.21 g of the 17β-(3-methoxy-phenyl)-isomer of Step A were reacted and the residue was chromatographed on silica and eluted with a 1—1 hexane-ethyl acetate mixture to obtain 698 mg of product B melting at 262° C.

EXAMPLE 13

11β-(4-dimethylamino-phenyl)-17α-(3-hydroxy-phenyl)-Δ$^{4,9}$-estradiene-17β-ol-3-one (product A) and 11β-(4-dimethylaminophenyl)-17β-(3-hydroxy-phenyl)-Δ$^{4,9}$-estradiene-17α-ol-3-one (product B)

STEP A: (1,2-ethanediyl)-cyclic acetal of 11β-(4-dimethylaminophenyl)-17α-[3-(tetrahydro-2H-2-pyranyloxy)-phenyl]-Δ$^9$-estrene-5α,17β-diol-3-one and 11β-(4-dimethylamino-phenyl)-17β-[3-(tetrahydro-2H-2-pyranyloxy)-phenyl]-Δ$^9$-estrene-5α,17α-diol-3-one Using the procedure of Example 10, 12.9 g of 3-bromophenyl tetrahydrofuran ether were reacted and the product was chromatographed on silica. Elution with a 80-20-1 methylene chloride-ethyl acetate-triethylamine mixture yielded 830 mg of the expected 17α-isomer and 1.55 g of the 17β-isomer. The latter melted at 224° C. after crystallization from ethyl acetate.

IR Spectrum (CHCl$_3$) of 17α-isomer: 17-OH: 3604 cm$^{-1}$; 5-OH: 3510 cm$^{-1}$; aromatic: 1610 cm$^{-1}$ 1517 cm$^{-1}$; 1562 cm$^{-1}$; 1580 cm$^{-1}$.

STEP B:

11β-(4-dimethylamino-phenyl)-17α-(3-hydroxy-phenyl)-Δ$^{4,9}$-estradiene-17β-ol-3-one (product A) and 11β-(4-dimethylamino-phenyl)-17β-(3-hydroxy-phenyl)-Δ$^{4,9}$-estradiene-17α-ol-3-one (product B)

4.5 ml of 2N hydrochloric acid were added to a solution of 890 mg of 17α-isomer of Step A in 9 ml of tetrahydrofuran, and after stirring at room temperature for 90 minutes, the mixture was poured into aqueous sodium bicarboate solution. The mixture was extracted with ethyl acetate and the organic phase was washed with aqueous sodium chloride and evaporated to dryness. The residue was chromatographed on silica and eluted with a 1—1 cyclohexane-ethyl acetate mixture to obtain 544 mg of product A with a specific rotation of $[\alpha]_D = +138° \pm 2°$ (c=1% in CHCl$_3$).

Using the same procedure, 800 mg of the 17β-isomer of Step A and 8 ml of 2N hydrochloric acid were reacted and crystallization of the extraction residue from a methanol-ethyl acetate mixture yielded 500 mg of product B with a specific rotation of $[\alpha]_D = +163° \pm 3°$ (c=0.33% in CHCl$_3$).

EXAMPLE 14

11β-(4-dimethylamino-phenyl)-17α-phenyl-Δ$^{1,3,5(10)}$-estratriene-3,17β-diol and its 17β-phenyl isomer

STEP A:
11β-(4-dimethylamino-phenyl)-Δ$^{4,9}$-estradiene-3,17-dione

A mixture of 1 g of 3,3-(1,2-ethanediyl)-cyclic acetal of 11β-(4-dimethylamino-phenyl)-Δ$^9$-estrene-5α-ol-17-one, 30 ml of ethanol and 5 ml of 2N hydrochloric acid was stirred at room temperature for 1 hour and was neutralized with triethylamine. The mixture was concentrated to a small volume and was extracted with methylene chloride. The organic phase was dried and evaporated to dryness and the residue was chromatographed on silica. Elution with a 95-5 methylene chloride-acetone mixture yielded 588 mg of product which was taken up in 2 ml of ether to obtain 510 mg of the expected product melting at 166° C.

STEP B:
11β-(4-dimethylamino-phenyl-Δ$^{1,3,5,(10)}$-estratriene-3-ol-17-one 8.9 g of palladium hydroxide with magnesium were added to a solution of 8.9 g of the product of Step A in 225 ml of methanol and the mixture was refluxed for one hour and was filtered. The filtrate was evaporated to dryness and the residue was chromatographed on silica. Elution with a 1—1 mixture of ether-ethyl acetate containing 1% of the triethylamine yielded 8.9 g of resin which was crystallized from an ethyl acetate-isopropyl ether mixture to obtain 5.1 g of the expected product melting at 256° C.

STEP C:
11β-(4-dimethylamino-phenyl)-17α-phenyl-Δ$^{1,3,5(10)}$-estratriene-3,17β-diol and its 17β-phenyl isomer 1 ml of a solution of 5.25 ml bromobenzene in 50 ml of anhydrous tetrahydrofuran was added to 1.45 g of magnesium turnings and the mixture was heated to 50° C. After the reaction ceased, the rest of the bromobenzene solution was added dropwise over 45 minutes at 60° C. The mixture was stirred at 60° C. for 30 minutes to obtain a solution of titrating 0.9N.

2 g of cerium chloride hydrate were heated for 2 hours at 140° C. under a reduced pressure and then 6 ml of tetrahydrofuran were added at room temperature. The mixture was stirred for 2 hours and then cooled to 0° C. after which 10 ml of the magnesium solution were added. The mixture was stirred at 0° C. for 2 hours and then a solution of 700 mg of the product of Step B in 8 ml of tetrahydrofuran was added. The mixture was stirred under an inert atmosphere at 0° C. for one hour and was then poured into aqueous ammonium chloride. The mixture was extracted with ethyl acetate and the organic phase was washed with water, dried and evaporated to dryness under reduced pressure. The residue was taken up in methylene chloride and isopropyl ether was added to recover 540 mg of raw product. The latter was crystallized from ethanol to obtain 266 mg of 11β-(4-dimethylamino-phenyl)-17α-phenyl-Δ$^{1,3,5(10)}$-estratriene-3,17β-diol melting at 277° C. and having a specific rotation of [α]$_D$= −286±3.5 (c=1% in CHCl$_3$). The crystallization mother liquors were chromatographed on silica and eluted with a 8-2 toluene-ethyl acetate mixture to obtain 80 mg of the 17β-phenyl isomer which was crystallized from an isopropyl ether-ethyl acetate mixture to obtain 73 mg of the 17β-phenyl isomer melting at 120° C.

IR Spectrum (CHCl$_3$) of 17α-phenyl: OH: 3597 cm$^{-1}$; aromatic: 1615 cm$^{-1}$-1580 cm$^{-1}$-1559 cm$^{-1}$-1520 cm$^{-1}$-1500 cm$^{-1}$.

IR Spectrum (CHCl$_3$) of 17β-phenyl: OH: 3599 cm$^{-1}$; aromatic 1614 cm$^{-1}$-1583 cm$^{-1}$-1560 cm$^{-1}$-1520 cm$^{-1}$-1498 cm$^{-1}$.

EXAMPLE 15

11β-,17α-bis-(4-dimethylamino-phenyl)-Δ$^{1,3,5(10)}$-estratriene-3,17β-diol

Using the procedure of Step C of Example 14, 33 ml of a solution of 1N 4-dimethylamino-phenyl magnesium bromide were reacted with a solution of 2 g of the product of Step B of Example 14 in 40 ml of tetrahydrofuran and after stirring for one hour at 3° C., the mixture was poured into aqueous ammonium chloride solution. The mixture was vacuum filtered and the solutions were taken up in a 1—1 mixture of methylene chloride and ethanol. The mixture was refluxed and vacuum filtered to obtain 1.57 g of the expected product melting at 206° C. The filtrate was extracted with ethyl acetate and the organic phase was washed with water, dried and evaporated to dryness. The residue was chromatographed on silica and eluted with a 9-1 methylene chloride-ethyl acetate mixture to obtain 420 mg of product which was crystallized with the 1.57 g obtained above from an ethanol-chloroform mixture to obtain 1.8 g of the expected product melting at 208° C. and having a specific rotation of [α]$_D$= −314°±4° (c=1% in pyridine).

EXAMPLE 16

11β-(4-dimethylamino-phenyl)-17α-(4-hydroxy-phenyl)-Δ$^{1,3,5(10)}$-estratriene-3,17β-diol

STEP A:
11β-(4-dimethylamino-phenyl)-17α-(4-tetrahydro-2H-2-pyranyloxy)-phenyl]-Δ$^{1,3,5(10)}$-estratriene-3,17β-diol Using the procedure of Example 9, 8.3 g of 4-(2′-RS-tetrahydropyranyloxy)-1-bromo-benzene and 1 g of magnesium were reacted to obtain a solution titrating 0.85N.

Using the procedures of Step A of Example 2, 2.5 of cerium chloride in 12 ml of tetrahydrofuran, 18 ml of the magnesium solution and 0.97 g of the product of Step B of Example 14 were reacted to obtain after concentration 5 g of raw product. The latter was chromatographed on silica and eluted with a 7-3 petroleum ether (b.p.=40°-70° C.)-ethyl acetate mixture to obtain 0.332 g of the expected product.

STEP B:
11β-(4-dimethylamino-phenyl)-17α-(4-hydroxy-phenyl)-Δ$^{1,3,5(10)}$-estratriene-3,17β-diol Using the procedure of Step B of Example 2, 0.307 g of the product of Step A in 6 ml of methanol and 0.6 ml of 2N hydrochloric acid were reacted to obtain 0.205 g of the expected product melting at >360° C. and after crystallization from a 1—1 methylene chloride-ethanol mixture had a specific rotation of [α]$_D$= +323.5°±3.5° (c=1% in pyridine).

Analysis: C$_{32}$H$_{37}$NO$_3$; molecular weight=483.65. Calculated: %C 79.47, %H 7.71, %N 2.89. Found: %C 79.3, %H 7.9, %N 2.8.

EXAMPLE 17

11β-(4-dimethylamino-phenyl)-17-(4-hydroxy-phenyl)-Δ$^{1,3,5(10),16}$-estratetraene-3-ol Using the procedure of Step B of Example 2, 0.15 g of the product of Step B of Example 16, 3 ml of methanol and 0.31 ml of 12N hydrochloric acid were reacted to obtain 0.166 g of raw product which was chromatographed on silica. Elution with a 1—1 mixture of petroleum ether (b.p.=40°-70° C.) and ethyl acetate yielded the expected product which was dried at 150° C.

Analysis: $C_{32}H_{35}NO_2$; molecular weight=465.65. Calculated: %C 82.54, %H 7.57, %N 3.00. Found: %C 81.4, %H 7.6, %N 2.9.

EXAMPLE 18

11β-[4-(2-dimethylamino-ethoxy)-phenyl]-17α-(4-hydroxy-phenyl)-Δ$^{4,9}$-estradiene-17β-ol-3-one STEP A: (1,2-ethanediyl)-cyclic acetal of 11β-[4-(2-dimethylamino-ethoxy)-phenyl]-17α-[4-(tetrahydro-2H-2-pyranyloxy)-phenyl-]-Δ$^9$-estrene-5α,17β-diol-3-one and its 17β-isomer Using the procedure of Step A of Example 2, 7.74 g of cerium chloride in 30 ml of tetrahydrofuran, 30 ml of the magnesium solution of Example 16 and 2.05 g of the (1,2-ethanediyl) cyclic acetal of Example 13 of European Patent 0,097,572 were reacted to obtain 8.2 g of a mixture of products which were chromatographed on silica. Elution with ethyl acetate containing 4% of triethylamine yielded 1.03 g of the 17α-hydroxy compound. Elution with an 8-2 methanol −0.05M aqueous ammonium acetate yielded 1.34 g of the 17β-hydroxy compound.

STEP B: 11β-[4-(2-dimethylamino-ethoxy)-phenyl]-17α-(4-hydroxyphenyl)-Δ$^{4,9}$-estradiene-17β-ol-3-one Using the procedure of Step B of Example 2, 1.25 g of the 17β-hydroxy compound of Step A, 13 ml of methanol and 0.95 ml of 2N hydrochloric acid were reacted to obtain 0.968 g of raw product which was crystallized from methanol and dried at 120° C. to obtain the desired product melting at ≃160° C. and having a specific rotation of [α]$_D$= +87±1.5 (c=1% in chloroform).

Analysis: $C_{34}H_{41}NO_4$; molecular weight=527.71. Calculated: %C 77.38, %H 7.83, %N 2.65. Found: %C 77.3, %H 7.6, %N 2.6.

EXAMPLE 19

11β-[4-(2-dimethylamino-ethoxy)-phenyl]-17-(4-hydroxy-phenyl)-Δ$^{4,9,16}$-estratriene-3-one

Method A 1.5 ml of 2N hydrochloric acid were added to a solution of 0.629 g of the 17α-hydroxy compound of Step A of Example 18 in 3 ml of tetrahydrofuran and after stirring for 30 minutes, the mixture was poured into aqueous sodium bicarbonate. The mixture was extracted with ethyl acetate and the organic phase was washed with water, dried and evaporated to dryness at 40° C. under reduced pressure. The residue was chromatographed on silica and eluted with a 95-5 methanol-aqueous 0.05M ammonium acetate mixture to obtain 0.277 g of the expted product.

METHOD B

A mixture of 0.422 g of the compound of Step B of Example 18 in 3 ml of tetrahydrofuran and 3 ml of 2N hydrochloric acid was heated at 50° C. under an inert atmosphere for 90 minutes and after cooling to room temperature, the mixture was poured into aqueous sodium bicarbonate. The mixture was extracted with ethyl acetate and the organic phase was washed with water, dried and evaporated to dryness at 40° C. under reduced pressure. The 0.392 g of residue was chromatographed on silica and eluted with a 7-3 ethanol-aqueous 0.05M ammonium acetate mixture to obtain the expected product with a specific rotation of [α]$_D$= +190°±3° (c=1% in CHCl$_3$).

Analysis: $C_{34}H_{39}NO_3$: molecular weight=509.69. Calculated: %C 80.1, %H 7.7, %N 2.75. Found: %C 79.7, %H 7.8, %N 2.6.

EXAMPLE 20

11β-[4-(2-dimethylamino-ethoxy)-phenyl]-17α-(4-hydroxy-phenyl)-Δ$^{1,3,5(10)}$-estratriene-3,17β-diol Using the procedure of Example 2, Step A, a mixture of 8.9 g of cerium chloride in 40 ml of tetrahydrofuran, 30 ml of 0.8N trimethylsilyloxyphenyl magnesium bromide in tetrahydrofuran and 2.36 g of 11β-[4-(2-dimethylamino-ethoxy)-phenyl]-Δ$^{1,3,5(10)}$-estratriene-3-ol-17-one [prepared as in European patent No. 0,097,572] were reacted to obtain 8.25 g of raw 17-(trimethylsilyloxy) product. 3.3 g of the said product were dissolved in 22 ml of methanol and after adding 4.35 g of silica, the mixture was stirred at room temperature for 3 hours. 1.8 ml of triethylamine were added and the mixture was filtered. The filtrate was evaporated to dryness at 40° C. under reduced pressure. The 2.638 g of residue were chromatogrphed on silica and eluted with a 90-10-0.5 methylene chloride-methanol-ammonium hydroxide mixture to obtain the desired product which after crystallization from methanol melted at 308° C. and had a specific rotation of [α]$_D$= −131°±2.5° (c=0.25% in ethanol).

Analysis: $C_{34}H_{41}NO_4$; molecular weight=527.31 on the product dried at 130° C. Calculated: %C 77.38, %H 7.83, %N 2.65. Found: %C 77.4, %H 7.9, %N 2.6.

EXAMPLE 21

11β-[4-(2-dimethylamino-ethoxy)-phenyl]-17-(4-hydroxy-phenyl)-Δ$^{1,3,5(10),16}$-estratetraene-3-ol Using the procedure of Step B of Example 2, 0.353 g of the product of Example 20 in 7.5 ml of methanol, 3 ml of tetrahydrofuran and 7.85 ml of 2N hydrochloric acid were reacted to obtain 0.356 g of raw product which was chromatographed on silica. Elution with a 9-1 methanol-aqueous 0.05M ammonium acetate and then a 90-10-0.5 methylene chloride-methanol-sodium hydroxide mixture yield the expected product which had a specific rotation of [α]$_D$= −135°±2.5° (c=1% in ethanol).

Analysis: $C_{34}H_{39}NO_3$ (on the product dried at 150° C.). Calculated: %C 80.1, %H 7.7, %N 2.75. Found: %C 79.8, %H 7.7, %N 2.6.

PHARMACOLOGICAL STUDY

A. Anti-proliferative activity against the increase of mammary Tumoral cells MCF-7

The cell culture line MCF-7 was maintained in culture in SVF (1) medium at 37° C. in a humid atmosphere containing 5% $CO_2$. The cells at subconfluence were collected by trypsination (0.05% trypsine, 0.02% EDTA) then rinsed by gentle centrifiguation. A sample of the cells in suspension was counted by the Malassez cell. To study the increase, the cells resuspended in SVF medium were innoculated at a rate of 30,000 cells per well in a multiwell plate (24 wells per 2.5 $cm^2$) 24 hours after the innoculation (Day 0), the test compound was added to the medium in an ethanolic solution (final ethanol concentration is 0.1%) a concentration of $10^{-6}M$. The control wells received the same concentration of ethanol. The mediums were totally renewed at 48 hours. At the end of the experiment (Day 6), the medium was aspirated and the cells were immediately fixed by 150 μl of methanol after a dose of ADN. The anti-proliferative activity of the products was determined by the capacity to inhibit ADN increase.

ADN is dosed by a fluorimetric method using DABA (3,5-diamino benzoic acid). 150 μl of DABA was added to each well and the plates were incubated for 45 minutes at 56° C. and then 1.5 ml of 1N hydrochloric acid was added. The fluoresence was measured with a fluorimeter (excitement length 400 nM-length of emission wave 500 nM). The amount of ADN per well was evaluated with respect to a standard scale obtained by treating under the same conditions an ADN standard of the calf thymus. The concentration in nM which inhibit by 50% the increase in the MCF 7 cells or $CI_{50}$ was determined in the same manner with the results of the following Table.

| Product of Example | $CI_{50}$ in nM |
|---|---|
| 2 | 500 |
| 3 | 800 |
| 4 | 400 |
| 5 | 1000 |
| 6 Product A | 50 |
| 6 Product B | 50 |

The medium for culture of calf fetal serum (SVF) was prepared as follows: MEM medium (minimal essential medium) to which was added non-essential amino acids (GIBCO), peni-strepto (penicillin 100 U/ml, streptomycine 0.1 mg/ml), 0.1% fungizone, 50 ng/ml of insulin and a 10% final concentration of calf fetal serum free of endrogenic steroids.

B. Activity toward hormonal receptors

The first test was on the progesterone receptors of rabbit uterus in which immature rabbits weighing about 1 kg received a cutaneous application of 25 g of estradiol and 5 days after treatment, the animals were sacrificed. The cutaneous was removed, weighed and homogenized at 0° C. with a Potter Teflon-glass ina buffered solution. TS (Tris 10 mM, 0.25M Saccharose, HCl, pH 7.4) (1 g of tissue per 50 ml of TS). The homogenate was ultracentrifuged at 105,000 g×90 minutes at 0° C. The surnageant samples were incubated at a time at (t) 0° C. with a constant concentration (T) of tritiated product (R) which is 17,21-dimethyl-19-nor-$\Delta^{4,9}$-pregnadiene-3,20-dione in the presence of increasing concentrations from 0 to $2500 \times 10^{-9}M$ or cold R or cold progestenone or cold test compound. The concentration of bound tritiated R was measured for each incubate by absorption technique on dextran carbon.

The second test was a glucocrticoid receptor test on rat thymus in which male rats of the Sprague Dawley EOPS strain weighing 160 to 200 g were surrenalectomized. 4 to 8 days after this ablation, the animals were killed and the thymus was removed and homogenized at 0° C. in a buffered TS solution. (Tris 10 mM, 0.25M saccharose, 2 mM dithiothreitol, HCl pH 7.4) with a Potter tetrafluoroethylene-glass (1 g of tissue per 10 ml/TS). The homogenate was ultracentrifuged at 105,000 for 90 minutes at 0° C. and the surnageant samples were incubated at 0° C. for a time t with a constant concentration T of tritiated dexamethasone in the presence of increasing concentrations ($0-2500 \times 10^{-9}M$) or cold dexamethasone or cold test compound. The concentration B of bound tritiated dexamethasone was measured for each incubate by carbon-dextran absorption technique.

The relative affinity of the bond (ARL) was calculated in the same for the receptors. One traced the following 2 curves: the percentage of bond tritiated hormone B/T as a logarithmic function of the concentration of the cold reference hormone and B/T as a logarithmic function of the concentration of the cold test compound. Using the equation $$I_{50} = \left( \frac{B}{T} \max. + \frac{B}{T} \min. \right)$$

B/T max. = % of bound tritiated hormone for one incubation of tritiated hormone at concentration (T)

B/T min. = % of bound tritiated hormone for one incubation of tritiated hormone at a concentration T in the presence of a great excess of cold hormone ($2500 \times 10^{-9}M$).

The intersections of $I_{50}$ lines and the curves permit an evaluation of the hormone concentration of the cold reference (CH) and the cold test compound (CX) which inhibited by 50% the bounding of tritiated hormone to the receptor. The ARL of the test compound was determined by the equation.

$$ARL = 100 \times \frac{CH}{CX}$$

and the following results were obtained.

| Time of incubation at 0° C. | Progestogen | | Glucocorticoid | |
|---|---|---|---|---|
| | 2H | 24H | 2H | 24H |
| Products of Example | | | | |
| 1 | 48 | 259 | 94 | 68 |
| 2 | 32 | 183 | 61 | 58 |
| 4 | 51 | 264 | 65 | 69 |
| 6 | 33 | 35 | 133 | 97 |
| 7 | 32 | 150 | 71 | 57 |
| 9 | 22 | 110 | 39 | 40 |
| 10 | 47 | 189 | 106 | 112 |
| 11 (Product A) | 38 | 230 | 56 | 45 |
| 11 (Product B) | 12 | 49 | 47 | 40 |
| 12 (Product A) | 24 | 131 | 90 | 76 |
| 13 (Product A) | 34 | 122 | 153 | 145 |

-continued

| Time of incubation at 0° C. | Progestogen 2H | Progestogen 24H | Glucocorticoid 2H | Glucocorticoid 24H |
|---|---|---|---|---|
| 13 (Product B) | 1,9 | 1,7 | 76 | 63 |
| 14 | 5 | 67 | 98 | 129 |

The results of the above Table show that the products of Examples 1 to 4 particularly have a very marked affinity for glucocorticoid and progesterone receptors. These results show that the compounds have agonist or antagonist activity for glucocorticoids and progesterones.

Various modifications of the compounds and method of the invention may be made without departing from the spirit or scope thereof and it is to be understood that the invention is intended to be limited only as defined in the appended claims.

What is claimed is:

1. A compound selected from the group consisting of compounds of the formula

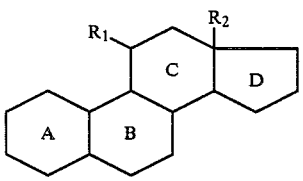

wherein $R_1$ is an organo of 1 to 18 carbon atoms optionally containing at least one heteroatom connected to the C ring by a carbon atom, $R_2$ is methyl or ethyl, the A and B rings are selected from the group consisting of

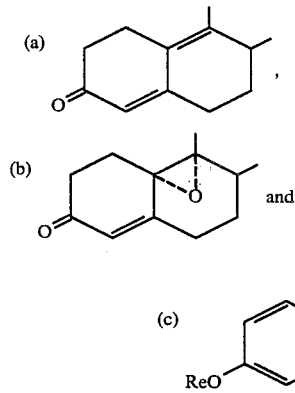

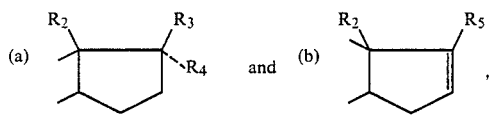

Re is selected from the group consisting of hydrogen, optionally substituted alkyl of 1 to 6 carbon atoms and acyl and the D ring is selected from the group consisting of one of $R_3$ and $R_4$ is selected from the group consisting of hydroxy, protected hydroxy, acyl and alkoxy and the other is an optionally substituted aryl, $R_5$ is an optionally substituted aryl and their non-toxic, pharmaceutically acceptable salts with acids and bases with the proviso that when the A and B rings are

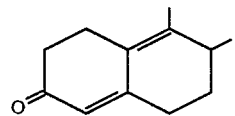

$R_1$ is

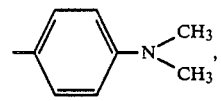

$R_2$ is methyl, $R_3$ is —OH and $R_4$ is phenyl.

2. A compound of claim 1 wherein $R_1$ is optionally substituted aryl.

3. A compound of claim 1 wherein the A and B rings are

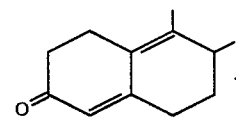

4. A compound of claim 1 wherein $R_3$ is —OH or methoxy and $R_4$ is optionally substituted aryl.

5. A compound of claim 1 selected from the group consisting of 11β,17α-bis-[4-dimethylamino-phenyl]-Δ⁴,⁹-estradiene-17β-ol-3-one and 11β-[4-dimethylamino-phenyl]-17α-(3-methoxy-phenyl)-Δ⁴,⁹-estradiene-17β-ol-3-one.

6. A glucocorticoid and progesterone antagonistic composition comprising a glucocorticoid and progesterone antagonistically effective amount of at least one compound of claim 1 and an inert pharmaceutical carrier.

7. A composition of claim 6 wherein $R_1$ is optionally substituted aryl.

8. A composition of claim 6 wherein the A and B rings are

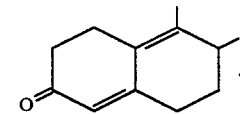

9. A composition of claim 6 wherein $R_3$ is —OH or methoxy and $R_4$ is optionally substituted aryl.

10. A composition of claim 6 wherein the active compound is selected from the group consisting of 11β,17α-bis-[4-dimethylamino-phenyl]-Δ⁴,⁹-estradiene-17β-ol-3-one and 11-[4-dimethylamino-phenyl]-17α-(3-methoxy-phenyl)-Δ⁴,⁹-estradiene-17β-ol-3-one.

11. A method of inducing glucocorticoid and progesterone antagonistic activity in warm-blooded animals comprising administering to warm-blooded animals a glucocorticoid and progesterone antagonistically effective amount of at least one compound of claim 1.

12. A method of claim 11 wherein $R_1$ is optionally substituted aryl.

13. A method of claim 11 wherein the A and B rings are

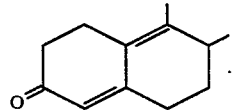
14. A method of claim 11 wherein $R_3$ is —OH or methoxy and $R_4$ is optionally substituted aryl.
15. A method of claim 11 wherein the active compound is 11β,17α-bis-[4-dimethylamino-phenyl]-$\Delta^{4,9}$-estradiene-17β-ol-3-one and 11β-[4-dimethylamino-phenyl]-17α-(3-methoxy-phenyl)-$\Delta^{4,9}$ estradiene-17β-ol-3-one.
* * * * *